United States Patent [19]

McArdle

[11] Patent Number: 5,645,880
[45] Date of Patent: *Jul. 8, 1997

[54] PROTEIN-POLYSACCHARIDE COMPLEX COMPOSITION AND METHOD OF USE

[76] Inventor: Blaise McArdle, 17 Leonard St., Annisquam, Mass. 01930

[ * ] Notice: The term of this patent shall not extend beyond the expiration date of Pat. No. 5,591,473.

[21] Appl. No.: 579,595

[22] Filed: Dec. 26, 1995

Related U.S. Application Data

[63] Continuation-in-part of Ser. No. 523,162, Sep. 5, 1995, Pat. No. 5,591,473, which is a continuation-in-part of Ser. No. 263,001, Jun. 17, 1994, abandoned, which is a continuation-in-part of Ser. No. 89,268, Jul. 8, 1993, abandoned.

[51] Int. Cl.$^6$ .............................. A23B 4/20; A23L 1/05; A23L 3/3472
[52] U.S. Cl. ..................... 426/327; 426/331; 426/573; 426/574; 426/575; 426/577; 426/654
[58] Field of Search ..................... 426/573, 575, 426/577, 615, 641, 643, 650, 654, 327, 331, 574

[56] References Cited

U.S. PATENT DOCUMENTS

| | | |
|---|---|---|
| 4,376,133 | 3/1983 | Farnand . |
| 4,447,412 | 5/1984 | Bilton . |
| 4,656,702 | 4/1987 | Morley et al. . |
| 4,754,027 | 6/1988 | Applegren . |
| 4,996,063 | 2/1991 | Inglett . |
| 4,997,671 | 3/1991 | Spanier . |
| 5,021,248 | 6/1991 | Stark et al. . |
| 5,126,143 | 6/1992 | Nakashima et al. . |
| 5,160,742 | 11/1992 | Mazer et al. . |
| 5,182,130 | 1/1993 | Haralampu et al. . |
| 5,294,457 | 3/1994 | Jenkins et al. . |

FOREIGN PATENT DOCUMENTS 9319615  10/1993  WIPO .

*Primary Examiner*—Arthur L. Corbin
*Attorney, Agent, or Firm*—Aaron B. Retzer

[57] ABSTRACT

Food products are preserved or stabilized against deterioration of organoleptic properties during storage by contacting the food products with an aqueous solution of a stabilizing composition containing at least one stabilizing acid and a protein-polysaccharide complex composition including at least one water-soluble polysaccharide and at least one substantially water-insoluble protein. Methods of preparation of the stabilizing composition and numerous methods of use of the protein-polysaccharide complex composition in the preservation of a variety of perishable seafood or other food products are also provided.

28 Claims, No Drawings

PROTEIN-POLYSACCHARIDE COMPLEX COMPOSITION AND METHOD OF USE

CROSS-REFERENCE TO RELATED APPLICATIONS

This application is a continuation-in-part of a application Ser. No. 08/523,162 filed on Sep. 5, 1995, now U.S. Pat. No. 5,591,473, which is a continuation-in-part of a application Ser. No. 08/263,001 filed on Jun. 17, 1994, now abandoned, which is a continuation-in-part of a application Ser. No. 08/089,268, filed on Jul. 8, 1993, now abandoned.

FIELD OF THE INVENTION

This invention relates generally to food preserving composition containing an acid and a protein complex composition, methods of preparation of a food preserving composition and uses of the composition for preserving or rejuvenating organoleptic properties of food including seafood.

BACKGROUND OF THE INVENTION

The taste of many food products severely diminishes during storage at either room temperature or during refrigeration. For instance, since seafood is extremely perishable in nature it must be eaten soon after catching or must be frozen to prevent spoilage. Only a few days after cooking, the meat of refrigerated lobsters and other crustaceans becomes rubbery in texture and their taste rapidly deteriorates from the desirable taste of fresh seafood. Another particularly difficult food to preserve is a fish fillet. Fresh fish fillets usually possess a shelf-life of only a few days after the fillet has been prepared. It would be extremely desirable to develop a process for preserving all types of food products by extending their shelf-lives while maintaining the desirable organoleptic qualities such as texture, taste and smell of the food products.

Proteins or prolamines, such as zein, have many utilities due to their amphoteric nature. Proteins have been used in in the past in a wide variety of applications including in the production of paper coatings, grease-resistant coatings, laminated boards, solid color prints, printing inks, food coatings, and microencapsulants. Prolamines are substantially insoluble in water and in alcohol but are soluble in alcohol-water mixtures.

It is an object of the present invention to produce a mixture of a stabilizing acid and a water soluble complex containing both a substantially water insoluble protein and a polysaccharide, the mixture displaying beneficial characteristics of both proteins and polysaccharides for use as a food preservative.

Another object of the present invention is the preservation of perishable food products, including seafood, against both weight loss and deterioration of desirable organoleptic qualities of the food occuring from periods of storage.

A further object of the present invention is to furnish a process for rejuvenating organoleptic properties of food that have deteriorated during storage.

These objectives are obtained by impregnating or coating the food products with a combination of an acid and a protein complex formed by impregnating or coating a polysaccharide with a substantially water-insoluble protein.

Still other objects and advantages of the invention will in part be obvious and will in part be apparent from the specification.

SUMMARY OF THE INVENTION

In accordance with the invention edible products, including seafood products, are preserved or stabilized against deterioration of organoleptic properties during storage by contacting the food products with an aqueous solution of a stabilizing composition containing at least one acid and a protein-polysaccharide complex composition including at least one water-soluble polysaccharide and at least one substantially water-insoluble protein. Methods of preparation of the stabilizing composition and numerous methods of use of the protein-polysaccharide complex composition in the preservation of a variety of perishable seafood and other food products are also provided.

DETAILED DESCRIPTION OF THE PREFERRED EMBODIMENTS

The composition of the present invention can be effectively used in preserving the desirable organoleptic qualities or properties of many edible products, including seafood, over extended periods of storage under a variety of temperature conditions. However, the present stabilizing compositions are not limited thereto and they may be used to treat aged, pickled or cured meats, fruits and vegetables. In accordance with the present invention any edible food product, including but not limited to: meats, vegetables, fruits, nuts, and seafood including fresh and processed fish, fish fillets, lobsters, crabs, shrimp, crawfish, mackerel, sardines, herring, salmon, cod, bass, trout, octopus and the like, is treated by contacting the edible surface of the food product with an aqueous solution containing the food stabilizing composition as described herein.

The food stabilizing or preserving compositions of the present invention, hereinafter referred to as food preserving or stabilizing agents, stabilize and preserve the organoleptic qualities of these food products while canned or during storage at non-refrigerated, refrigerated or freezing temperatures. The organoleptic qualities of the food products preserved by treatment of the food with the stabilizing or preserving agent of the present invention include the retention of fresh taste, texture, odor and color while maintaining uniform flavor throughout the food product. The room temperature, refrigerated and frozen shelf-life of these stabilized food products is significantly extended after treatment with the stabilizing agents of the present invention. It is believed that the food stabilizing agents stabilize the oils present in the foods treated with these agents against degradation. Furthermore the present food stabilizing agents serve to minimize or prevent significant weight loss in the treated food product during periods of refrigerated or non-refrigerated storage.

The food stabilizing or preserving agents of the present invention contain at least one stabilizing acid and a protein-polysaccharide complex composition prepared from the combination of at least one water-soluble polysaccharide, at least one substantially water-insoluble protein and at least one acidulant.

The protein-polysaccharide complex (PPC) composition used as a component of the food stabilizing agent of the present invention includes a water-soluble polysaccharide, a substantially water-insoluble protein and optionally, but preferrably, an acidulant. The polysaccharides are water-soluble, and are generally recognized as safe (G.R.A.S.) by the U.S. Food and Drug Administration. In general, the water-soluble polysaccharides are plant-derived polysaccharides and related materials such as pectin.

Examples of polysaccharides that can be used to prepare the PPC compositions include, but are not limited to water-soluble cellulose derivatives, seaweed polysaccharides such as alginate and carrageenin, seed mucilaginous polysaccharides, complex plant exudate polysaccharides such as gum arabic, tragacanth, guar gum, pectin, ghatti and the like, and microbially synthesized polysaccharides such as xanthan gum. In a preferred embodiment, the polysaccharides are guar gum, pectin, gum arabic and mixtures thereof.

The polysaccharide preferably is present in an amount ranging between about 90% to 99.5% by weight of the total PPC composition, preferably in an amount ranging between about 95% to 99% by weight of the total PPC composition. The total PPC composition is defined as the total weight of the protein and polysaccharide components.

Similarly, the protein can be any protein that is predominately or substantially water-insoluble, however, vegetable proteins are advantageously utilized due to their availability. In-general, the vegetable protein is a prolamine. A prolamine is a cereal-derived protein that is insoluble in water, absolute alcohol or neutral solvents and soluble in dilute (80%) alcohol. Suitable examples of prolamines include, but are not limited to, corn-derived prolamine or zein, barley-derived prolamine or hordein and wheat-derived prolamine or gliadin.

The substantially water-insoluble protein is present in an amount ranging between about 0.5% to 10% by weight of the total PPC composition, preferably in an amount ranging between about 1% to 5% by weight of the total PPC.

In a preferred embodiment of the invention, the vegetable protein or prolamine used in the composition is zein or corn gluten. Zein is extracted from corn or maize. PPC compositions containing zein are used to form odorless, tasteless, clear, hard and almost invisible films.

Sixteen amino acids have been isolated from zein including glutamic acid or glutamine, leucine, proline, alanine, phenylalanine, isoleucine, serine, tyrosine and asparagine. The remaining seven amino acids are present in amounts of less than 3% by weight. Of the eight amino acids that are necessary for protein synthesis in the human body, zein has virtually no lysine or tryptophan.

Zein is extracted from corn gluten by physical separation means as opposed to chemical separation means. Whole corn zein contains a heterogeneous mixture of disulfide linked aggregates. Commercial extraction results in a product with a molecular weight of 25,000 to 35,000. Zein contains a high proportion of hydrocarbon group side chains and has a high percentage of amide groups present with a relatively low amount of free carboxylic acid groups.

Relatively small amounts of at least one organic, food-grade pH adjusting compound in the form of an acid, hereinafter referred to as an acidulant, are preferably used to lower the pH of the aqueous polysaccharide solutions during preparation of the PPC compositions to between 1 to 11.5, preferably about 3.8 to 8.5. The acidulants enhance the water dispersibility of the PPC compositions, thereby facilitating reconstitution of the protein-polysaccharide complex compositions in water. Although any pH adjusting acidic compound is useful in the present invention, including inorganic acids such as carbonic acid, sulfuric acid, hydrochloride acid and the like, it is preferable to utilize organic acids, preferably $C_1$ to $C_{20}$ organic acids. Suitable organic acidulants include, but are not limited to: citric acid, malic acid, adipic acid, tannic acid, lactic acid, ascorbic acid, acetic acid, fumaric acid and the like and mixtures thereof, as well as salts thereof such as Na, K, and Ca salts. In a preferred embodiment, citric acid is used.

The acidulants employed in the production of the PPC compositions are used in an amount between about 0.25% to 5% by weight of the total PPC compositions during the preparation of the PPC composition, preferably in an amount between about 0.5% to 1% by weight. The acidulant is preferably added to the water of an aqueous organic solvent system prior to addition of the organic components although it may be added contemporaneously with other organic components.

A PPC composition is prepared by dissolving the substantially water-insoluble protein or prolamine in an aqueous organic solvent system containing the acidulant to form a protein solution. The soluble polysaccharide is then added to the protein solution to form a protein-polysaccharide complex in solution. While the solvent can be separated or evaporated from the solution to yield the final, dry reconstitutable protein-polysaccharide complex (PPC) composition, it is often preferable to retain the complex in solution for subsequent application to food products.

The aqueous organic solvent system is a mixture containing at least one organic solvent in water. Suitable organic solvents include, but are not limited to, alcohols such as ethyl alcohol and isopropyl alcohol; edible glycols such as propylene glycol and certain polyethylene glycols; and, ketones such as acetone. In a preferred embodiment of the invention, the aqueous organic solvent system is either aqueous ethyl alcohol or aqueous isopropyl alcohol. Alcohols generally can hold up to six grams of zein in solution for each 100 milliliters of alcohol.

The desired ratio of water to organic solvent in the aqueous organic solvent system is dependent on factors such as the miscibility of the solvent in the water and the amount of protein to be dissolved. When the organic solvent system is aqueous ethyl alcohol or aqueous isopropyl alcohol, the amount of water generally ranges between about 10% to 40% by weight and the amount of alcohol generally ranges between about 60% to 90% by weight. More preferably, the amount of water in such systems is between about 25% to 35% and the amount of alcohol is between about 65% to 75%.

The substantially water-insoluble protein or prolamine is added to the aqueous organic solvent system in an amount between about 100 and 300 grams of prolamine per liter of aqueous organic solvent system, more preferably in an amount between about 120 to 240 grams per liter. The dissolution is carried out at a temperature between about 20° C. (ambient room temperature) and about 60° C., preferably about 30° C. using conventional agitation methods to form a protein solution. Soluble polysaccharide in minute fiber or particulate form is then admixed with the protein solution to form a PPC in solution.

In a preferred embodiment, instead of pure zein, a protein containing gluten such as corn gluten can be directly added into the aqueous organic solvent system, preferably containing the acidulant, thus passing the zein protein portion of the gluten into solution while the deprotenated non-zein remainder of the gluten can be separated by vacuum filtering or other standard separation techniques. An incidental amount of up to 100%, preferably up to 10% by weight of deprotenated gluten can be present in the recovered in admixture with the protein-polysaccharide complex without adversely affecting the properties of the complex. Zein produced in this manner does not undergo extraction utilizing benzene/toluene extracting agents as in many prior art production practices, and thus the zein retains both natural oils and colorants providing beneficial organoleptic stabilizing properties to the food preserving agent subsequently produced in the present invention.

It is important that the substantially water-insoluble protein or prolamine thoroughly impregnate the soluble polysaccharide particles during the process of admixing the soluble polysaccharide with the protein solution. The aqueous organic solvent system used to prepare the protein solution should wet the soluble-polysaccharide particles so that the hydrophilic soluble polysaccharide particles are impregnated or coated with the hydrophobic protein to form the PPC solution.

The admixing process is carried out until a complete uniform mixture is attained. In general, the process is carried out at a temperature between about 20° C. and 60° C., preferably between about 20° C. and 25° C. for a time period of between about 10 and about 30 minutes, preferably between about 10 and 15 minutes. The PPC solution is agitated during the admixing process by conventional agitation methods including, but not limited to, manual shaking, mechanical shaking, magnetic stirring, mechanical stirring or a combination thereof.

Additives that promote impregnation may be added at any point during the admixing process. These additives can also affect the dispersibility and film forming characteristics of the PPC composition. Suitable additives include, but are not limited to, food grade detergents and emulsifiers in amounts up to 5%, preferably 0.125% to 5%, by weight of the protein complex. Exemplary additives are polysorbates, edible vegetable oils and egg albumin.

The solvent may be separated or evaporated to yield a protein-polysaccharide complex composition, that is, particulate polysaccharide impregnated or complexed with a protein that can be reconstituted in water for application as a component of the food preserving or preservative agent. Any number of solvent removal techniques may be used including, but not limited to, vacuum drying, centrifugation, evaporation, freeze drying, air drying, convection oven drying or a combination thereof.

It is preferred that the solvent removal technique be one that does not require the use of excessive or prolonged heat that will oxidatively darken the product. Although oxidative darkening has little effect on the utility of the product it may affect its appeal and desirability. One preferred method of extracting the solvent is vacuum drying which safety removes and recovers the solvent while drying the product to provide the PPC composition.

The protein-polysaccharide complex composition provided in accordance with the invention can be further processed by grinding or milling to a desired mesh particle size for use in tablets, granules, powders, pellets, extrusions, flours and the like. In one embodiment, the composition can be formed into a powder for subsequent introduction into a food processing liquid.

As a second component of the food stabilizing agent of the present invention a stabilizing acid, hereinafter referred to as a stabilizing acid, is added to the finally formed PPC composition to create the food preserving or stabilizing agent. The stabilizing acid is added either into the PPC solution or with dry PPC into a water solution. Once the PPC composition in either dry or solution form has been prepared and admixed with the stabilizing acid, the composition can be used as a food and seafood preserving agent. The stabilizing acid enhances the food stabilization properties of the food stabilizing agents when used in conjunction with the PPC compositions. The stabilizing acids useful in the formation of the food preserving agent of the present invention, include any organic food grade acids, preferably $C_1$ to $C_{20}$ organic acids. Suitable organic acids include, but are not limited to: citric acid, malic acid, adipic acid, tannic acid, lactic acid, ascorbic acid, acetic acid, fumaric acid and the like and mixtures thereof, as well as salts thereof such as Na, K, and Ca salts. In a preferred embodiment, a mixture of ascorbic acid and citric acid is used.

In the preparation of the food preservative agent, the stabilizing acids are used in a stabilizing effective amount between about 20% to 300% by weight of the PPC composition, preferably in an amount between about 100% to 250% by weight. The stabilizing acid is preferably added to the water of in an amount ranging between about 0.5 to 50 grams of stabilizing acid per aqueous gallon of food preserving agent, preferably 10 to 30 grams of stabilizing acid per aqueous gallon of food preserving agent. In a preferred embodiment, a combination of citric acid and ascorbic acid is used.

The PPC composition component is preferably added to the water of in a stabilizing effective amount ranging between about 0.5 to 50 grams of dry PPC composition per aqueous gallon of food preserving agent, preferably 10 to 30 grams of dry PPC composition per aqueous gallon of food preserving agent. Aqueous solutions containing the above-recited amounts are stabilizing effective amounts of the food preserving agent, however a broader range individual components may be useful in view of the wide variety of food products to which the preserving agent is applicable.

It is understood that the PPC in solution can be mixed with the stabilizing acid directly into water for application onto the food products or the particulate or powdered protein-polysaccharide complex can be admixed with the stabilizing acid in water for contact application onto edible, food products.

An aqueous solution of the food preserving agent of the present invention containing approximately three pounds of preserving agent can used to effectively stabilize or rejuvenate up to 10,000 pounds of most edible products including lobster meat, fish fillets, shrimp, other seafood products, vegetables, fruits and meats. However, the amount of food preserving agent used can vary widely with respect to each food product being treated. From as little as one pound up to 50 pounds or more of food preserving agent can be used for each 10,000 pounds of food to be treated.

The food preserving agent of the present invention is also useful in rejuvenating or restoring the taste and texture of previously stored, refrigerated, frozen or canned food products, particularly meat and seafood products by contacting by washing the food products with an aqueous solution containing a stabilizing amount of the food preserving agent.

The food preserving agent can be applied to the various food and seafood products in a variety of application manners depending on the actual product to be preserved. Basically all products can be preserved, stabilized, or rejuvenated by simply contacting the food products with an aqueous solution containing the food preserving agent. Contacting includes spraying, dipping, rinsing, and freezing in ice or contacting with ice containing the food stabilizing agent. Crustaceans such as lobsters are preferably stored, cooked or boiled in an aqueous solution containing the food preserving agent generally for a contact time of 5 to 10 minutes.

In order to stabilize the food products against deterioration of organoleptic properties during storage it is necessary to contact the surface of the seafood or food product with the food preserving agent for a period of time sufficient to coat or impregnate the food product. Since various food product coat or adsorb coatings at different rates, application times for contacting food products with the food preserving agent vary but are readily apparent to one skilled in the art.

It is also often desirable to post-treat the edible products, after they have been in contact with the food preserving agent, with a dilute solution of a food grade acid or base, preferably an acid, typically in a 0.005 to 2% aqueous solution. This post-treatment process serves to firm the texture of the stabilized food product. A preferred post-treating agent is a 0.125% aqueous solution of acetic acid.

The following examples of preparation of the PPC composition and its use as a seafood preserving agent are presented for purposes of illustration only and are not to be construed to limit the scope of the invention described herein.

EXAMPLE 1

A 10% zein solution was prepared by dissolving 10 grams of zein in 90 grams of an aqueous isopropyl alcohol solution. The aqueous isopropyl alcohol solution contained 15% water by weight and 85% isopropyl alcohol by weight. Dissolution was carried out in a 500 ml beaker and the solution was initially stirred using a mechanical stirrer at a speed of over 100 rpm in order to fully wet the zein. Once all of the zein was dispersed, the stirring speed was reduced by about ½ for an additional five minutes to insure complete dissolution of the zein in the aqueous isopropyl alcohol solution. The ambient temperature was maintained at 22° C. throughout this procedure. Accordingly, a protein solution was provided.

Two hundred grams (200 g) of milled guar gum powder (fine-60 mesh, TIC GUMS, Belcamp, Md.) was slowly added to the protein solution with vigorous stirring using a mechanical stirrer at a speed of over 100 rpm. Manual stirring was started as the mixture thickened. Additional aqueous isopropyl alcohol was added as needed to attain a soupy appearance indicative of successful impregnation of the soluble guar gum particles by the zein solution. Agitation of this soupy liquid mixture was maintained for fifteen minutes.

The resulting PPC solution was dried under reduced pressure of 0.05 atmospheres. at a temperature of 60° C. using a lab-line Duo-Vac vacuum oven manufactured by LabLine Corp., Melrose Park, Ill. The resulting dried PPC composition was a yellowish-beige color and was milled to a granular form (80 mesh).

EXAMPLE 2

A soupy PPC solution containing was prepared as described in Example 1. After addition of the guar gum was complete, 20 grams of dried egg albumin (Henigson, Inc., White Plains, N.Y.) was added and dispersed completely. The solution was dried under reduced pressure at 60° C. using a Lab-Line Duo-Vac vacuum oven. The resulting PPC composition was a yellowish-beige color and was milled to a granular form.

EXAMPLE 3

Fifty grams (50 g) of citric acid was added to 0.675 kg of water used to prepare 4.5 kg of an 85:15 alcohol: water aqueous organic solvent system. Five hundred grams of zein was added to the aqueous organic solvent system in a suitable vessel. The aqueous organic solvent was kept in motion during the addition with the aid of a mechanical stirrer. Accordingly, a solution of 10% by weight of zein in aqueous alcohol was prepared.

Nine and one-half kg of guar gum was added to the 10% zein solution with mixing in a Stokes Heavy Duty sigma-type blender. After about 30 minutes of continuous mixing, the mass was homogeneous, slightly tan and had a wet, sand-like consistency. The mass was dried in an explosion-proof drier to yield a protein-polysaccharide complex.

EXAMPLE 4

An aqueous solution of the food preserving agent of the present invention was prepared by adding 10 grams of citric acid and 10 grams of ascorbic acid with 10 grams of PPC composition prepared in accordance with the procedure of Example 3 into a 10 gallon agitated mixer filled with water.

EXAMPLE 5

The food preserving agent as prepared in accordance with the procedure of Example 4 was utilized to preserve lobster meat in the following manner. An aqueous solution containing the ratio of food preserving agent as prepared in accordance with the procedure of Example 4 was elevated to a boil at a temperature of a 100° C. Ten live lobsters were placed into the boiling water and cooked for approximately 15 minutes until the lobsters were fully cooked. The lobster meat was removed from the lobsters and was frozen. Nine days later the frozen lobster meat was thawed and reheated. The lobster meat exhibited a firm texture but was not rubbery in texture and displayed an excellent taste comparable to freshly cooked lobster.

EXAMPLE 6

Ten pounds of freshly caught, unprocessed herring were soaked at room temperature for approximately two minutes in the aqueous solution of the food preserving agent as prepared in accordance with the procedure of Example 4. The ten pounds of herring were deheaded, gutted, cleaned and then rinsed with an aqueous solution containing 0.125% of acetic acid. The cleaned herring was then stored under refrigerated conditions at 33° F. For 48 hours, after which the fish displayed no deterioration of color, texture or odor. Five pounds of the herring was then was frozen at −50° F. and after twenty days the fish was thawed and displayed no deterioration in color, texture and smell. The thawed herring was cooked and a taste test was performed between the thawed, cooked herring treated by the preserving agent of the present invention and cooked, untreated freshly caught herring. The cooked, treated herring was significantly better in taste, odor and appearance in comparison to the cooked, fleshly caught herring both immediately after cooking and after 48 hours of refrigeration at 33° F.

EXAMPLE 7

Fifty pounds of freshly caught, oily, deep water Dover sole were divided into two groups of equal weight. One group of twenty-five pounds was soaked at room temperature for approximately two minutes in the aqueous solution of the food preserving agent as prepared in accordance with the procedure of Example 4 and twenty-five pounds of Dover sole remained untreated. The fish in both groups was then processed normally into fillets. The treated fillets were bright in color and free from the normal odor associated with deep water Dover sole. The fillets from the untreated fish were oily and displayed an unpleasant odor.

Both the treated and untreated fillets were boxed and refrigerated at 33° F. for 48 hours and thereinafter the treated fillets displayed no significant weight loss while the untreated fillets displayed a 14% weight loss. Samples from each group of fillets were then wrapped in plastic and flash frozen in liquid nitrogen and stored for 30 days at a temperature of −60° F. After removal from the freezer the treated fillets displayed no sign of freezer-burn while the untreated fillets were badly freezer-burned. After all samples were thawed the treated samples appeared fresh and firm in color and texture, while the untreated fillets displayed undesirable organoleptic qualities in odor and texture. A portion of each sample was then cooked by microwave or steaming. The cooked, treated fillets displayed the characteristics of cooked, fresh flounder having no substantial weight loss and excellent taste while the cooked, untreated fillets were essentially unpalatable.

EXAMPLE 8

A mixture of dried fruits including blueberries, cranberries, raisins, figs, dates, and apricots were washed for one minute in a hot bath of the aqueous solution of the food preserving agent as prepared in accordance with the procedure of Example 4, rinsed with an aqueous solution containing 0.125% of acetic acid, and dried in a conventional drum drier. The treated dried fruit was stored at room temperature and periodically examined over a period of four months. All of the treated fruits maintained their color, texture and odor without losing their free flowing characteristics. The treated fruit showed no significant weight losses over the storage time and retained its excellent taste and flavor. Untreated dried fruits undergoing the same test procedure became tacky and bunched together in the packages. The untreated dried fruit was hard to remove from the packages and the oil present in the fruit showed signs of deterioration.

The food preserving agent of the present invention is also useful in preserving and stabilizing other food products including nuts such as walnuts, pecans, peanuts, pistachios and walnuts, as well as dried beans, rice, coffee, poultry such as chicken and turkey, and red meats such as steak, ground beef, ham, pork, and the like. Subjecting these or other food products to washes containing the food preserving agent of the present invention allows these products to retain their natural flavor and texture while extending their shelf life and substantially reducing weight loss during storage.

It will thus be seen that the objects set forth above, among those made apparent from the preceding description, are efficiently attained and, since certain changes may be made in the described product, and in carrying out the above process, and in the construction set forth without departing from the spirit and scope of the invention, it is intended that all matter contained in the above description shall be interpreted as illustrative and not in a limited sense.

It is also to be understood that the following claims are intended to cover all of the generic and specific features of the invention herein described and all statements of the scope of the invention which, as a matter of language, might be said to fall therebetween.

Particularly, it is to be understood that in said claims, ingredients or compounds recited in the singular are intended to include compatible mixtures of such ingredients wherever the sense permits.

What is claimed is:

1. A food preserving composition for treating edible products to maintain or refurbish desirable organoleptic qualities thereof comprising: a mixture of at least one stabilizing acid and a protein-polysaccharide complex composition comprising: between about 90% to 99.5% by weight of a water-soluble polysaccharide impregnated with between about 10% to 0.5% by weight of a substantially water-insoluble protein.

2. The protein-polysaccharide complex composition of claim 1 wherein the water-soluble polysaccharide is selected from the group consisting of alginate, carrageenan, gum arabic, tragacanth gum, guar gum, pectin, ghatti gum, xanthan gum and mixtures thereof.

3. The protein-polysaccharide complex composition of claim 1 wherein the substantially water-insoluble protein is a prolamine.

4. The protein-polysaccharide complex composition of claim 1 wherein the substantially water-insoluble protein is zein.

5. The protein-polysaccharide complex composition of claim 1 wherein the composition further includes at least one additive for promoting impregnation of the water-soluble polysaccharide by the protein.

6. The protein-polysaccharide complex composition of claim 1 wherein the substantially water-insoluble protein is hordein or gliadin.

7. The protein-polysaccharide complex composition of claim 1 wherein the water-soluble polysaccharide comprises guar gum and the substantially water-insoluble protein comprises zein.

8. The protein-polysaccharide complex composition of claim 1 further comprising:
   an acidulant in an amount ranging between about 0.25% to 5% by weight of the protein-polysaccharide complex composition.

9. The protein-polysaccharide complex composition of claim 8 wherein the acidulant is selected from the group consisting of tannic acid, lactic acid, ascorbic acid, acetic acid, citric acid, malic acid, adipic acid, fumaric acid, mixtures thereof and salts thereof.

10. The protein-polysaccharide complex composition of claim 8 wherein the acidulant is citric acid.

11. The food preserving composition of claim 1 wherein the stabilizing acid is an organic food grade acid or a salt thereof.

12. The food preserving composition of claim 11 wherein the stabilizing acid is selected from the group consisting of tannic acid, lactic acid, ascorbic acid, acetic acid, citric acid, malic acid, adipic acid, fumaric acid and mixtures thereof.

13. The food preserving composition of claim 11 wherein the stabilizing acid is present in an amount ranging between about 20% to 300% by weight of the protein-polysaccharide complex composition.

14. The food preserving composition of claim 11 wherein the stabilizing acid is citric acid.

15. The food preserving composition of claim 11 wherein the stabilizing acid is a mixture of citric acid and ascorbic acid.

16. The food preserving composition of claim 11 wherein the stabilizing acid is present in an amount ranging between about 100% to 250% by weight of the protein-polysaccharide complex composition.

17. A process for treating an edible product to maintain desirable organoleptic properties thereof during storage comprising:
   contacting the edible product with a stabilizing effective amount of an aqueous solution containing a food preserving agent comprising a mixture of a stabilizing acid and a protein-polysaccharide complex composition comprising between about 90% to 99.5% by weight of a water-soluble polysaccharide impregnated with between about 10% to 0.5% by weight of a substantially water-insoluble protein.

18. The process of claim 17 wherein the process further comprises the step of post-treating by contacting the edible food product with a dilute aqueous solution containing an organic food grade acid or base.

19. The process of claim 18 wherein the organic food grade acid is acetic acid.

20. The process of claim 17 wherein the edible food product is contacted by freezing in a solution containing the food preserving agent.

21. The process of claim 17 wherein the edible food product is seafood.

22. The process of claim 17 wherein the edible food product is lobster.

23. The process of claim 17 wherein the edible food product is fish.

24. The process of claim 17 wherein the edible food product is shrimp.

25. The process of claim 17 wherein the edible food product is a vegetable.

26. The process of claim 17 wherein the edible food product is a fruit.

27. The process of claim 17 wherein the edible food product is meat.

28. An edible food product preserved to maintain desirable organoleptic properties thereof during storage having a surface film formed from a preserving agent comprising:

a mixture of a stabilizing acid and a protein-polysaccharide complex composition comprising between about 90% to 99.5% by weight of a water-soluble polysaccharide impregnated with between about 10% to 0.5% by weight of a substantially water-insoluble protein.

* * * * *